United States Patent [19]

Vogler et al.

[11] Patent Number: 5,455,009
[45] Date of Patent: Oct. 3, 1995

[54] BLOOD COLLECTION ASSEMBLY INCLUDING CLOT-ACCELERATING PLASTIC INSERT

[75] Inventors: Erwin A. Vogler, Newhill, N.C.; Nicholas A. Grippi, Ramsey, N.J.; Jane C. Graper, Durham, N.C.

[73] Assignee: Becton, Dickinson and Company, Franklin Lakes, N.J.

[21] Appl. No.: 121,009

[22] Filed: Sep. 14, 1993

[51] Int. Cl.⁶ ........................................ B01L 3/00
[52] U.S. Cl. .................. 422/102; 422/73; 422/99; 422/101; 436/69; 435/2
[58] Field of Search ................ 422/102, 101, 422/73, 57, 99; 435/2; 436/69, 177

[56] References Cited

U.S. PATENT DOCUMENTS

| 4,131,549 | 12/1978 | Ferrara | 210/359 |
|---|---|---|---|
| 4,420,517 | 12/1983 | Ali | 428/35 |
| 4,770,779 | 9/1988 | Ichikawa et al. | 210/516 |
| 4,967,763 | 11/1990 | Nugent et al. | 128/763 |
| 5,064,541 | 11/1991 | Jeng et al. | 210/767 |
| 5,213,765 | 5/1993 | Kasai et al. | 422/102 |
| 5,236,604 | 8/1993 | Fiehler | 422/102 |
| 5,246,666 | 9/1993 | Vogler et al | 422/73 |
| 5,257,633 | 11/1993 | Vogler et al. | 128/763 |
| 5,326,535 | 7/1994 | Vogler et al. | 422/102 |

Primary Examiner—Donald E. Czaja
Assistant Examiner—Lien Tran
Attorney, Agent, or Firm—Richard E. Brown

[57] ABSTRACT

A blood collection assembly includes a tube, which may be glass or plastic, and a plastic insert therein. The insert has been plasma-treated to change the surface chemistry and render it clot activating.

10 Claims, 6 Drawing Sheets

BLOOD COLLECTION ASSEMBLY INCLUDING CLOT-ACCELERATING PLASTIC INSERT

BACKGROUND OF THE INVENTION

1. Field of the Invention

This invention relates to blood collection and, more particularly, relates to a plastic blood sample collection assembly.

2. Background

Blood samples are routinely taken in evacuated tubes, such as glass VACUTAINER® brand tubes (Becton, Dickinson and Company). One end of a double-ended needle is inserted into a patient's vein. The other end of the needle then punctures a stopper covering the open end of the VACUTAINER® tube so that the vacuum in the tube draws the blood sample through the needle into the tube. Using this technique, a plurality of samples can be taken using a single needle puncture of the skin. Plastic tubes have also been proposed for blood collection. Plastic offers a number of advantages over glass such as lower breakage, less weight in shipment, and easier disposal by incineration.

Blood collected in evacuated tubes often must be clotted prior to clinical examination. It is desirable to form a dense clot as rapidly and completely as possible to facilitate clean separation of the clot from the serum layer by centrifugation. To achieve this end, both plastic and glass blood collection tubes frequently employ a clot activator. Typical activators are diatomaceous earth and particles of inorganic silicates, or biochemicals such as ellagic acid, thrombin and thromboplastin. In one line of commercial blood collection tubes, for example, a coating of silicate particles in polyvinylpyrrolidone (PVP), a water soluble polymer) is affixed to the inside of the tube. When blood enters the tube, the PVP dissolves and silicate particles are released to initiate clotting. The PVP enters both the serum and clot.

A problem with particulate activators is that finely divided particles must be mixed by inversion, may not pellet completely with the clot and may thus contaminate the serum layer and interfere with certain blood analyses. In addition, particles suspended in the serum may foul automatic blood analysis instruments. On the other hand, soluble biochemical activators can be disadvantageous because these cannot be easily separated from either the serum or blood clot and can interfere with both chemical and hematological assays. In particular, for highly specialized applications, such as blood banking, it is advantageous to avoid either soluble activators or particulates in the cell mass of a blood clot because these cells are used in blood typing analyses. For this reason, samples for blood banking are routinely taken in glass tubes and rely on the clot activating property of the glass to induce clotting.

There is a need in the art of blood collection for equipment which provides an enhanced rate of blood coagulation without leaving any soluble or particulate material in the serum layer or in the clot on centrifugation, thus avoiding potential interference with clinical tests, and particularly in blood banking procedures. The present invention is directed to fulfilling this need.

SUMMARY OF THE INVENTION

A blood collection assembly includes a tube of glass or plastic having a bottom wall continuous with a side wall. The side wall defines an open end and the bottom wall defines a closed end. Together the bottom and side walls define an inside wall surface. The open end may be covered by a puncturable stopper and the tube may be evacuated. The assembly includes a plasma-treated plastic insert, preferably polystyrene (PS), within the interior volume of the tube. The insert may be of various shapes, such as a fin, funnel, disc, spring, or monofilament, and may be permanently or movably affixed to the tube wall or may rest on the tube bottom. An additive useful in blood separation or analysis procedures may be present in the tube or in the insert.

When a blood sample is taken in the assembly of the invention, the blood flows past and comes into contact with the plasma-treated plastic insert. This contact activates the clotting cascade.

Thus, the assembly of the invention retains the advantages of plastic and overcomes the disadvantage of poor and slow coagulation in plastic. The plasma treatment modifies the chemistry of the plastic insert to be clot-activating so that clotting is accelerated but no particulate or soluble clotting activators or binders are present to contaminate either the serum or the clot.

DETAILED DESCRIPTION

While this invention is satisfied by embodiments in many different forms, there will herein be described in detail preferred embodiments of the invention with the understanding that the present disclosure is to be considered as exemplary of the principles of the invention and is not intended to limit the invention to the embodiments illustrated and described. The scope of the invention will be measured by the appended claims and their equivalents.

The blood collection assembly of the invention may include any container having a closed end and an open end. Suitable containers are, for example bottles, vials, flasks and the like, preferably tubes. The invention will henceforth be described in terms of the preferred tube. The tube contains structure having a surface chemistry which activates clotting of blood and may optionally contain an additive useful in blood separation or analysis.

Figure 1:
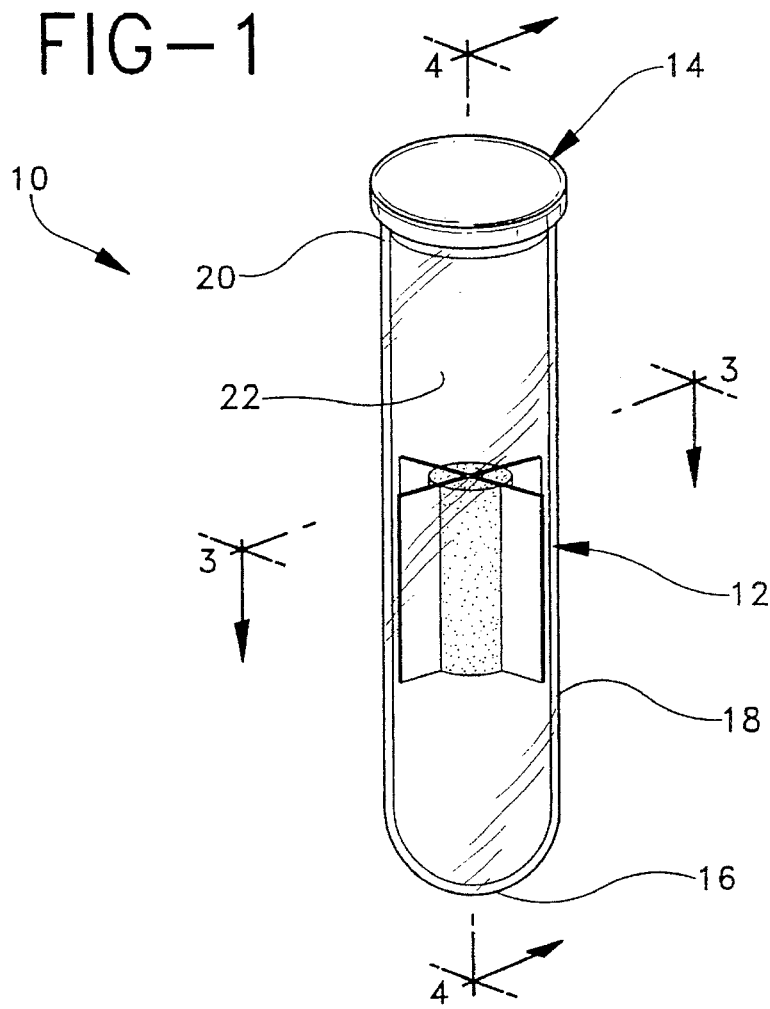
FIG. 1 is a perspective view of the blood collection assembly of the invention.

Adverting now the drawings, FIG. 1 illustrates a blood collection assembly 10 which includes a tube 12 and a puncturable stopper 14. Tube 12 has a bottom wall 16 and a side wall 18 defining an open end 20 into which the stopper 14 may be placed. Bottom wall 16, side wall 18 and stopper 14 enclose an interior volume 22 of the tube which preferably is evacuated. Evacuated tubes for blood collection are standard in the art. Tube 12 has an insert positioned in interior volume 22. The insert may simply rest on the bottom wall 16 of the tube or preferably may form an interference fit with the tube sidewall. The interference fit may be sufficiently tight so that the insert is stationary during centrifugation or preferably is a movable interference fit so that the insert descends during centrifugation.

Figure 2:
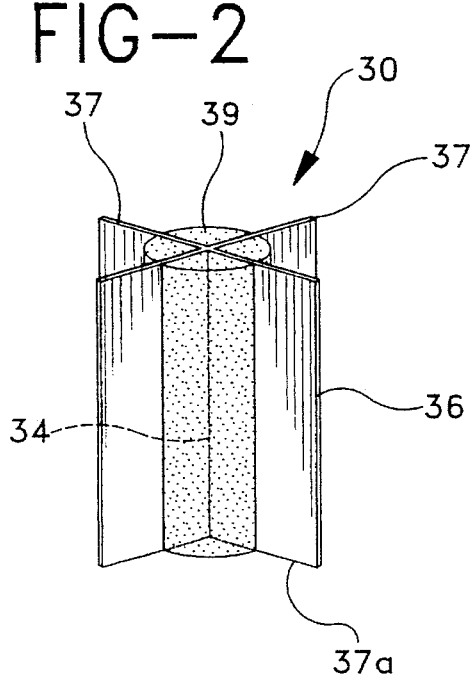
FIG. 2 is a perspective view of a preferred insert of the invention.
Figure 3:
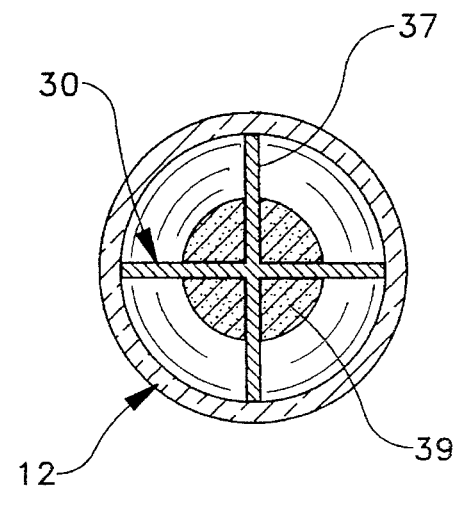
FIG. 3 is a sectional view of the insert of FIG. 2 taken along the line 3—3 thereof.

FIGS. 2 and 3 illustrate a preferred embodiment of the insert. (In FIGS. 2–11, elements which are the same or substantially the same as elements previously described are given the same reference number followed by a letter suffix.) In FIG. 2, an insert 30 is illustrated as a member having a plurality of fins 32 joined together at a common axis 34. Each fin has a longitudinal edge 36 and upper and lower transverse edges 37 and 37a respectively. While FIGS. 2 and 3 show insert 30 to have four fins, it is not intended to place any restriction on the number of fins. Likewise, the dimensions of the fins are limited only by the size of tube 10 into which the insert is to be placed. Preferably longitudinal edge 36 may be about 3 cm in length and transverse edges 37 and 37a may be about 0.5 cm each. Optionally a cavity 38 formed by two the fins may contain an additive 39, such as a thixotropic gel.

Figure 4:
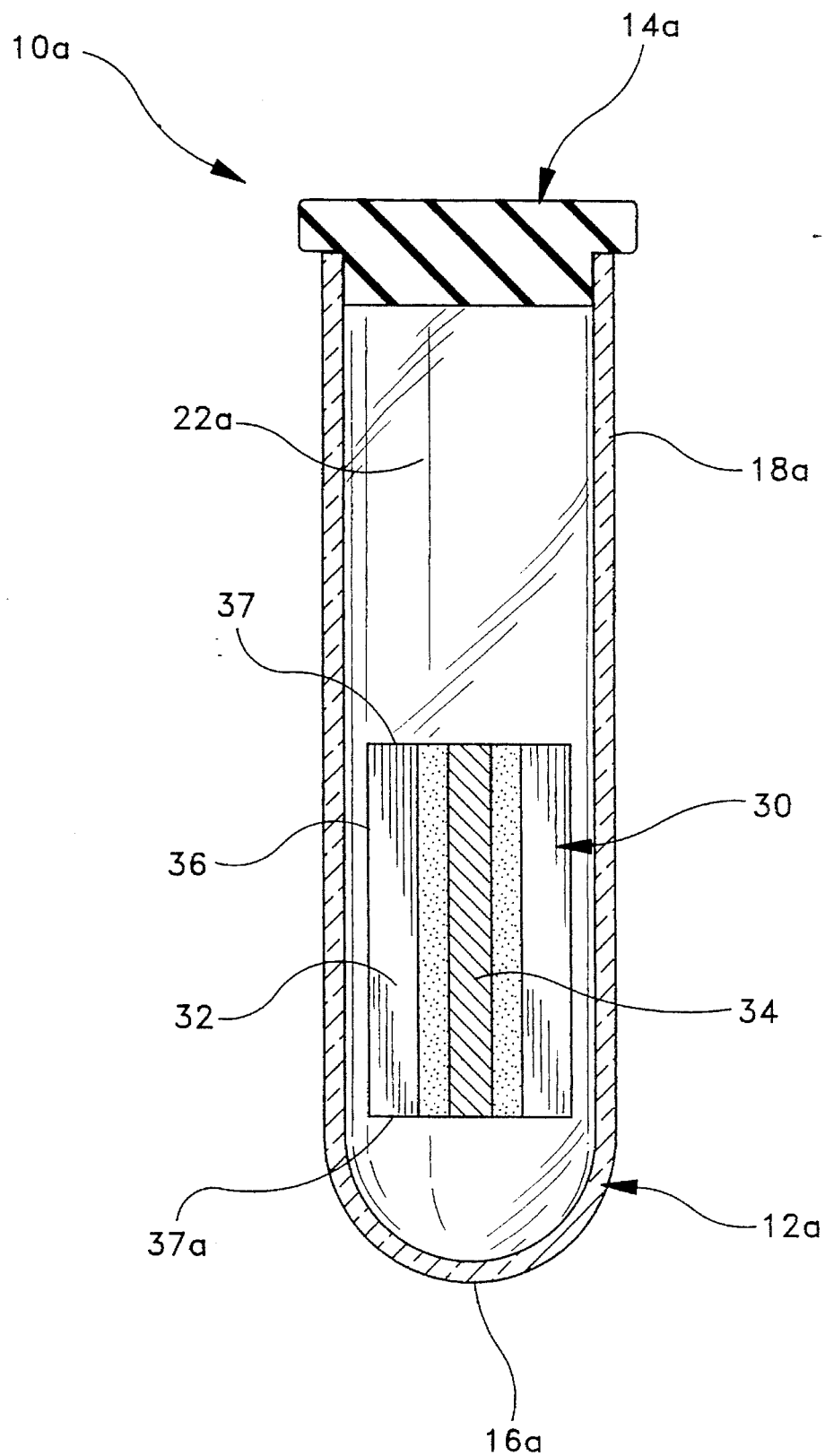
FIG. 4 is a vertical sectional view of the assembly of FIG. 1 taken along the line 2—2 thereof and showing the insert of FIGS. 2 and 3 in the interior thereof.

In FIG. 4, insert 30 of FIG. 2 is shown positioned in interior volume 22a of tube 10a by an interference fit between longitudinal edge 36 and side wall 18a. FIG. 4 shows the insert positioned toward the bottom of the tube, but the positioning of the insert is wholly optional and in general dictated by the projected end use of the collection assembly.

Figure 5:
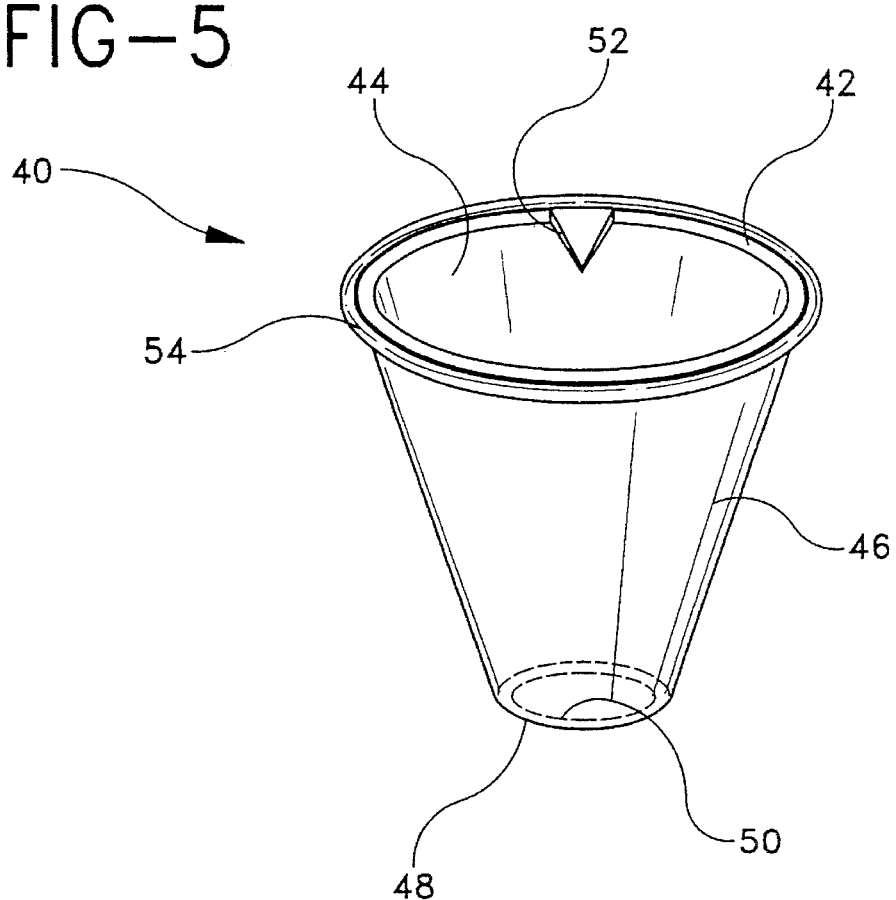
FIG. 5–7 illustrate an embodiment of the assembly of the invention showing a funnel shaped insert.
Figure 6:
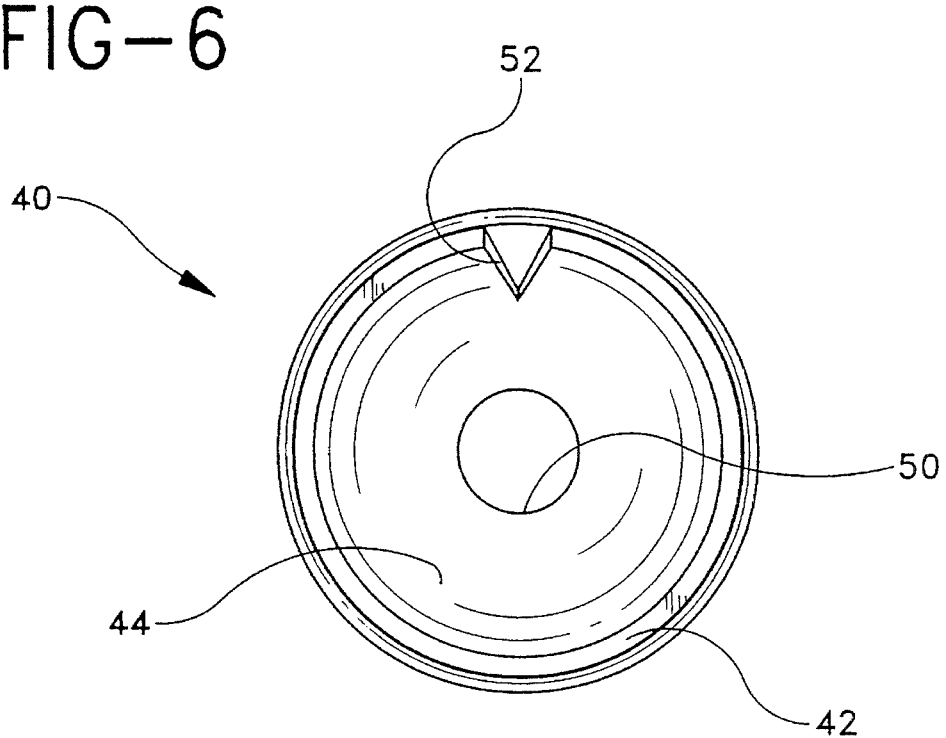
Figure 7:
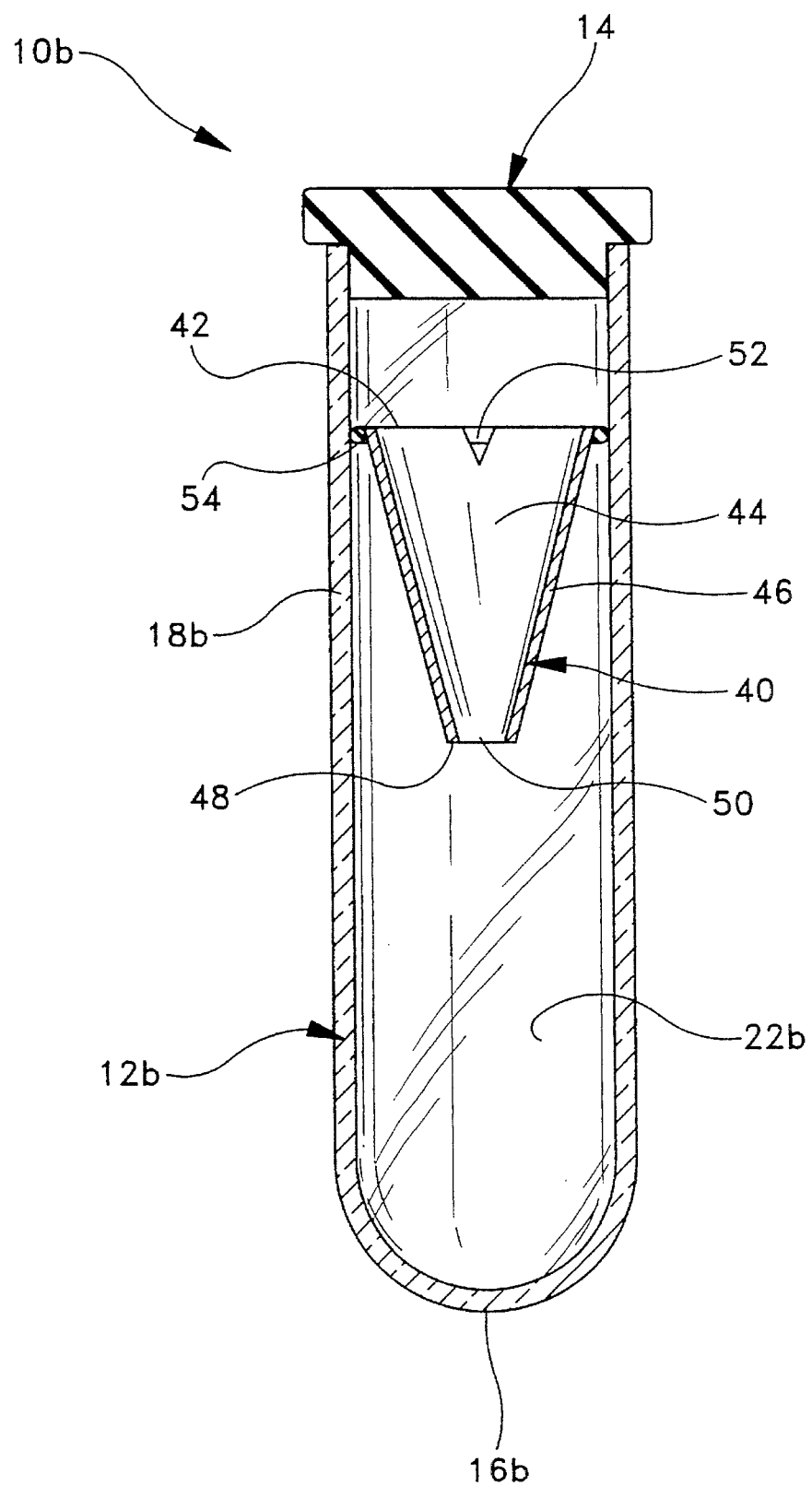

FIGS. 5 to 7 illustrate an embodiment of the invention in which the insert has the shape of a funnel. In FIGS. 5 and 6, a funnel shaped insert 40 has a substantially annular top edge 42 defining an open top end 44 and a tapered side wall 46 terminating at a substantially annular bottom edge 48 defining an open bottom end 50. Top edge 42 may have an optional notch 52 to serve as an air vent during use, and may optionally have an elastomeric ring seal 54 around top edge 42.

In FIG. 7, insert 40 of FIG. 5 is shown positioned in tube 12b and held in place against side wall 18b by elastomeric ring seal 54. Alternatively, insert 40 may be positioned (not shown) by an interference fit between side wall 18b and insert top edge 42. In still another means for affixing the insert to the tube wall, insert top edge 42 may have a plurality of integrally molded flanges (not shown in the drawings) protruding therefrom wherein the interference fit is established between the flanges and the tube wall. This arrangement leaves spaces between the insert and the tube wall for fluid flow.

Open ends 44 and 50 may be of any suitable size according to the particular application contemplated for the assembly. Preferably, open top end 44 may be about 0.5 to 2 cm in diameter and open bottom end 50 may be about 0.1 to 0.5 cm in diameter.

Figure 8:
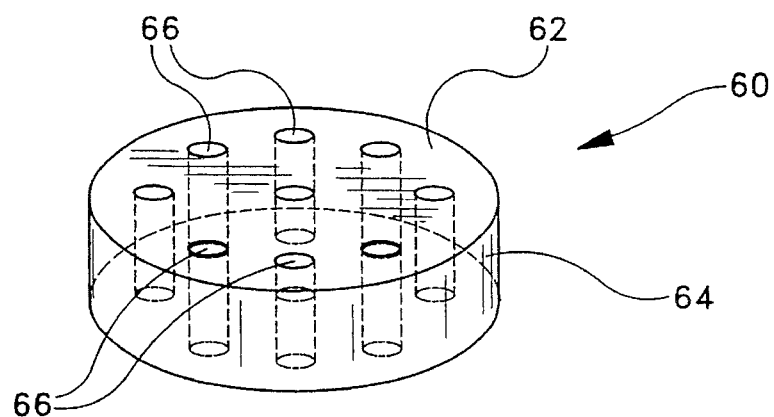
FIG. 8 illustrates an insert in the form of a disc.

The insert may also have the shape of a disc. The disc may be of any suitable shape. FIG. 8 illustrates a disc 60 which is substantially annular. Disc 60 has a top surface 62 and a side wall 64 and preferably is dimensioned so that the side wall forms an interference fit with the side wall of the tube. When an interference fit is used to position the annular disc in the tube, the disc may have a plurality of channels 66 therethrough for fluid passage and fluid contact with the plasma treated surface during use. Alternatively, the disc may have a shape, such as an ellipse, or the annular disc may have projections (not shown) from side wall 64 so that the interference fit is established only at a plurality of points around the side wall and spaces are present between the interference contact points for fluid passage. The thickness of the disc may be about 0.01 to 0.5, preferably about 0.1 to 0.2 cm. Channels 66, while shown in FIG. 8 to be substantially circular, may be of any shape, size and number. Thus the disc and channels together may be substantially in the form of a mesh or filter disc. An additive useful in blood separation or analysis may be located in the channels.

Figure 9:
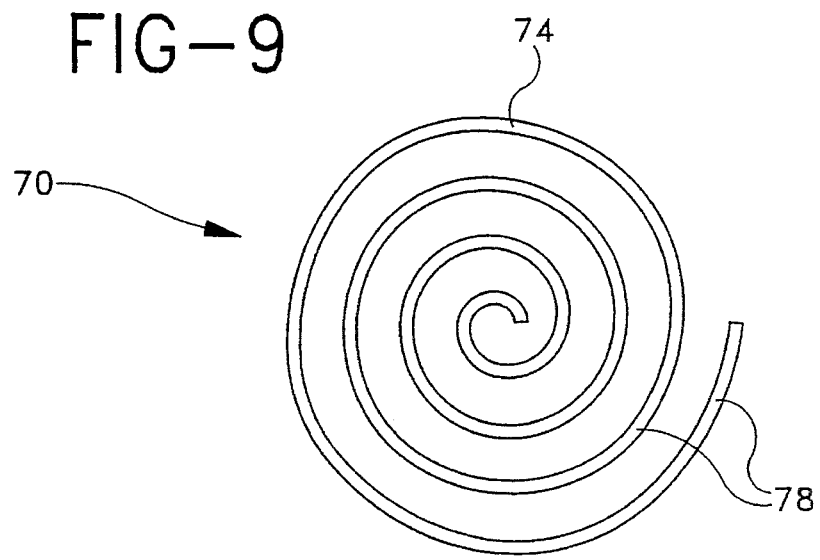
FIGS. 9 and 10 illustrate inserts in the form of a spring.
Figure 10:
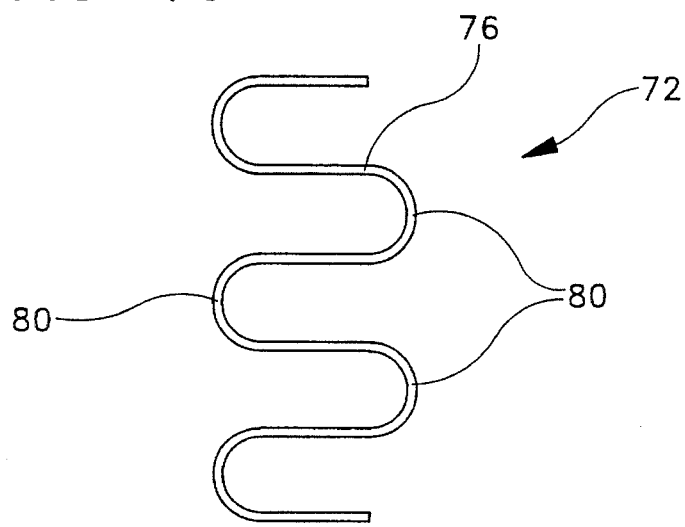

Another embodiment of the insert contemplated by the invention is a spring. FIG. 9 and 10 illustrate two of many suitable spring shapes 70 and 72 having coils 74 and 76 respectively. Springs 70 and 72 may conveniently be positioned by interference fits established between two or more points 78 and 80 on the coils and the inside wall of the tube.

Figure 11:
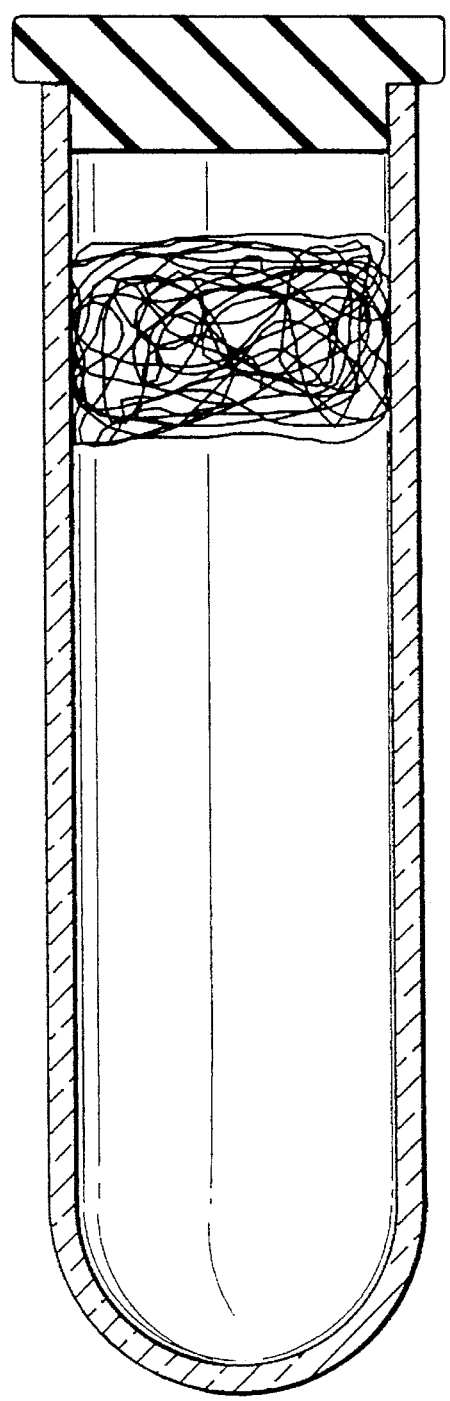
FIG. 11 illustrates an insert in the form of a wad of monofilament.

Another form of the insert is a wad of plasma-treated plastic monofilament which may be positioned by an interference fit as shown in FIG. 11.

The tube may be of glass or preferably plastic. Suitable plastics are polypropylene (PP), polyethylene terephthalate (PET) and polystryene (PS). While the tube maybe of any size, the invention is particularly well suited to evacuated blood collection tubes. These tubes are generally cylindrical, 50 to 150 mm in length and about 10 to 20 mm in diameter. The stopper may be of any elastomer, as is well known in the art of evacuated blood collection tubes. Likewise the insert may be of plastic, such as PET or preferably PS, and generally is manufactured by injection molding. Clot activation does not occur with PP or PS inserts which have not been plasma-treated. The insert may be integral with the tube and formed with the tube in a single molding operation.

In accordance with the invention, it has been found that treatment of the insert with a plasma results in a surprising increase in the rate of clotting of a blood sample. If additional plasma-treated surface area is desired, the inside wall of the tube itself may also be plasma-treated.

The plasma may be generated from any suitable process gas. A representative but not limiting list of suitable process gases includes nitrogen, ammonia, carbon dioxide, sulfur dioxide, air and oxygen wherein air and oxygen are preferred. The insert may be placed between the electrodes of a conventional plasma generator equipped with a pressure gauge, a gas inbleed and a vacuum connection. Suitable electrodes may be of any conducting material, although stainless steel and aluminum are preferred. The width and shape of the electrodes is not critical. Any suitable ionizing plasma may be used, as, for example, a plasma generated by a corona discharge or preferably a glow discharge.

A wide range of power settings, radio frequencies and duration of exposure of the plastic surface to the plasma may be used. Ranges for these parameters which provide advantageous results are DC or AC power levels up to 200 watts, from about 0.1 to about 50 megahertz and from about 0.1 to 30 minutes. Preferred ranges are 10–50 watts, 10–20 megahertz and 2–10 minutes respectively. Any gas pressure may be used, however, gas pressures are advantageously maintained at 5 mm of Hg or below in order to benefit from reduced voltage requirements. Ambient temperature for plasma generation is preferred. Further details are not needed by one skilled in the art for a full understanding of this aspect of the invention.

The plasma treatment results in introduction of polar functional groups into the surface of the plastic. The functional group depends on the process gas used to generate the plasma. For example, after plasma treatment, the surface may contain oxygen, nitrogen or sulfur atoms. These groups cause the plasma-treated surface to have a clot activating property similar to and even somewhat greater than that of glass. The examples show the accelerated clotting rates induced by the plasma-treated plastic surfaces relative to those of glass and untreated plastic.

The assembly may contain, depending on the projected end use, any of a variety of additives known to be useful in blood separation or analysis. A preferred additive is a thixotropic gel which, on centrifugation of the tube, migrates to the interface between the serum and the cells and serves for separation. Without wishing to be limited thereby, other conventional additives which may be included in the assembly are biochemicals such as thrombin, ellagic acid, or heparin or chemicals such as citric acid, EDTA, or oxalates.

In its preferred application, the assembly of the invention is used for collection of a blood sample and separation of the sample into a serum layer and a pellet of clotted cells. A patient sample is drawn through a double ended needle into the evacuated tube by puncture of the stopper. The sample comes into contact with the plasma- treated insert which activates the clotting mechanism. After allowing a few minutes for clotting, the tube is centrifuged. If a separator gel is located in the insert, as described above, it flows from the insert during centrifugation and comes to rest as a separation layer between the serum and the pellet. If the gel is supplied, as is conventional, in the bottom of the tube, it flows upward to separate the layers.

EXAMPLE I

General Procedure for Plasma Treatment

The inserts were subjected to an oxygen plasma for 10 minutes in a conventional planar diode system at about 50 mtorr pressure and 50 watts of 13.56 $MH_z$ radio frequency power. The inserts were placed in the bottom of 13×100 mm molded tubes. Glass and PET tubes without inserts served as controls.

EXAMPLE II

General Procedure for Testing Clot Activation

Clot activating properties of the plasma-treated assemblies of the invention were assessed by comparison of time required to clot whole porcine blood to that in untreated PET and glass tubes. Approximately 5 ml of citrated porcine blood (Environmental Diagnostics, Inc.) was dispensed into tubes and recalcified by addition of 1 ml of 0.2M $CaCl_2$ with mixing by five inversions. Clotting was allowed to proceed for 20 minutes in a water bath held at room temperature and the tubes were subsequently rotated on an inverting hematological rotator for a set time interval between 4 and 15 minutes. After the specified interval, tubes were centrifuged in a standard hematology centrifuge and a visual assay was used to assess the completion of clotting. Clotted blood was distinguished from non-clotted blood by the presence of a clear, fluid serum layer, cleanly separated from cells, that did not form a gelatinous fibrin clot even after standing for 1 hour. These tubes were rated with a (+) score. Incomplete clotting was obvious by the formation of a gelatinous fibrin clot above the pelleted cell layer and was rated with a (−) score. Ambiguous results were rated with a (±) score.

EXAMPLE III

A. Clot Activation of Porcine Blood Using Fin Type Inserts

Inserts having 4 fins (FIG. 2) were prepared from 3 ml PS film and oxygen plasma-treated according to Example I. The inserts were placed in the bottom of PET tubes and tested for clot activation according to Example II. The following results were obtained.

| Clot Time (min.) | Control Tubes | | Test Tubes |
| --- | --- | --- | --- |
| | Glass | PET | |
| 4 | − | − | − |
| 6 | − | − | − |
| 8 | ± | − | + |
| 10 | ± | − | + |
| 12 | + | − | + |
| 15 | + | − | + |

B. As described in A, the plasma-treated PS insert was placed in the bottom of PS and PP tubes and found to activate clotting in the same way as in PET tubes.

EXAMPLE IV

Clot Activation of Porcine Blood Using Funnel Type Inserts

A PS insert as illustrated in FIG. 5 was plasma-treated according to Example I and placed in the top of a PET tube. The tube was filled with porcine whole blood, tested for clot activation as in Example II, and observed after 35 minutes (45 minutes including centrifuge time). The serum was separated cleanly from the clot with no evidence of a plasma clot.

EXAMPLE V

Clot Activation of Whole Human Blood

A. With Fin Type Inserts

PET tubes containing fin-type PS inserts as described in Example III A and 5 ml freshly-drawn whole human blood were continuously rotated on a standard inverting hematology mixer. Clean separation of serum from clot was obtained in 10 minutes clot time.

EXAMPLE VI

A clot activating PS fin type insert was prepared as in Example III A and one section of the insert was filled with a conventional serum-cell separating thixotropic gel (Becton, Dickinson and Company). The insert was located in the upper portion of a PET tube and held in place by an interference fit. The tube was filled with porcine whole blood, allowed to clot for 35 minutes and centrifuged. The gel flowed downward during centrifugation and became located between the serum and clot, thus serving as a serum-cell separation.

This example shows that inserts can be simultaneously used as clot activators and vehicles to carry additives useful in blood analysis procedures.

What is claimed is:

1. A blood collection assembly comprising a container having a bottom wall, a side wall defining an open end, and an ionizing plasma-treated insert positioned inside of said container for activating clotting of blood, said insert being movably affixed to said side wall and forming an interference fit therewith such that said insert descends toward the bottom wall during centrifugation.

2. The assembly of claim 1 further comprising a stopper in said open end.

3. A blood collection assembly comprising a tube having a bottom wall, a side wall defining an open end, a stopper in said open end, and a plastic plasma-treated blood clot-activating insert in said tube, said insert being movably affixed to said side wall and forming an interference fit therewith such that said insert descends toward the bottom during centrifugation.

4. The assembly of claim 3 further comprising an additive in said tube.

5. The assembly of claim 3 wherein said insert is in the form of a fin.

6. The assembly of claim 3 wherein said insert is in the form of a funnel.

7. The assembly of claim 3 wherein said insert is in the form of a perforated disc.

8. The assembly of claim 3 wherein said insert is in the form of a wad of plastic monofilament.

9. A blood collection assembly comprising:
   a) a tube having a bottom wall and a side wall defining an open end;
   b) an elastomeric puncturable stopper in said open end, said bottom wall, side wall and stopper defining an interior volume of said tube, said interior volume being evacuated;
   c) an ionizing plasma-treated, clot activating, polystyrene insert positioned in the tube, said insert being movably affixed to said side wall and forming an interference fit therewith such that said insert descends toward the bottom wall during centrifugation.

10. A blood collection assembly comprising a tube having a bottom wall, a side wall defining an open end, a stopper in said open end, and an ionizing plasma-treated plastic blood clot-activating insert in said tube, said insert being affixed to said side wall and having the shape of a fin, funnel, perforated disc or wad of plastic monofilament.

* * * * *